US009724491B2

(12) United States Patent
Solar et al.

(10) Patent No.: US 9,724,491 B2
(45) Date of Patent: Aug. 8, 2017

(54) MICROCATHETER WITH DISTAL TIP PORTION AND PROXIMAL SOLUTION LUMEN

(75) Inventors: Ronald Jay Solar, San Diego, CA (US); Yoav Shaked, Moshav Mishmeret (IL); Glen Lieber, Poway, CA (US)

(73) Assignee: THERMOPEUTIX, INC., San Diego, CA (US)

( * ) Notice: Subject to any disclaimer, the term of this patent is extended or adjusted under 35 U.S.C. 154(b) by 813 days.

(21) Appl. No.: 13/079,866

(22) Filed: Apr. 5, 2011

(65) Prior Publication Data

US 2012/0259214 A1    Oct. 11, 2012

(51) Int. Cl.
  *A61M 25/00* (2006.01)
  *A61M 25/10* (2013.01)
  *A61M 25/01* (2006.01)

(52) U.S. Cl.
  CPC ....... *A61M 25/0068* (2013.01); *A61M 25/104* (2013.01); *A61M 2025/0039* (2013.01); *A61M 2025/0042* (2013.01); *A61M 2025/0177* (2013.01); *A61M 2025/0183* (2013.01); *A61M 2025/0186* (2013.01)

(58) Field of Classification Search
  CPC ...... A61M 25/0068; A61M 2025/0042; A61M 2025/0039; A61M 25/104; A61M 25/005; A61M 2025/0177; A61M 2025/0183; A61M 2025/0186; A61M 25/007; A61M 25/0026; A61M 25/01
  USPC ............. 604/529, 509, 508, 510, 523, 96.01
  See application file for complete search history.

(56) References Cited

U.S. PATENT DOCUMENTS

| 4,641,654 A * | 2/1987 | Samson .......... A61M 25/09025 600/434 |
| 5,833,652 A * | 11/1998 | Preissman et al. ............. 604/82 |
| 5,925,016 A * | 7/1999 | Chornenky et al. ....... 604/96.01 |
| 6,159,195 A | 12/2000 | Ha |
| 6,824,550 B1 * | 11/2004 | Noriega ........... A61B 17/32075 604/22 |
| 2001/0041905 A1 | 11/2001 | Yock |
| 2005/0075647 A1 | 4/2005 | Walters |
| 2006/0009740 A1 | 1/2006 | Higgins |
| 2006/0184099 A1 * | 8/2006 | Hong ..................... A61M 25/00 604/43 |
| 2007/0208368 A1 | 9/2007 | Katoh et al. |
| 2007/0213671 A1 * | 9/2007 | Hiatt ................... A61M 25/007 604/164.01 |
| 2007/0219578 A1 | 9/2007 | Solar et al. |
| 2007/0258903 A1 * | 11/2007 | Kleiner et al. ................. 424/9.3 |
| 2008/0234706 A1 * | 9/2008 | Sepetka et al. ............... 606/159 |
| 2009/0198153 A1 * | 8/2009 | Shriver ........................ 600/585 |

(Continued)

FOREIGN PATENT DOCUMENTS

JP    2004130110    4/2004

*Primary Examiner* — Bhisma Mehta
*Assistant Examiner* — Brandy S Lee
(74) *Attorney, Agent, or Firm* — Daniel J. Swirsky; Ricki L. Simon; AlphaPatent Associates Ltd.

(57) ABSTRACT

There is provided a microcatheter having a proximal solution lumen and a distal tip portion with a guidewire lumen. The microcatheter and methods of use thereof allows for introduction of solution into a vessel while manipulating the guidewire and/or the microcatheter itself. The solution may be a contrast solution, for viewing of the vessel, a therapeutic or diagnostic solution, or any other type of solution.

26 Claims, 8 Drawing Sheets

(56) References Cited

U.S. PATENT DOCUMENTS

2010/0069855 A1* 3/2010 Ross .................. A61M 25/0068
604/268
2010/0256616 A1 10/2010 Katoh et al.

* cited by examiner

MICROCATHETER WITH DISTAL TIP PORTION AND PROXIMAL SOLUTION LUMEN

FIELD OF THE INVENTION

The present invention is directed to a microcatheter having a tip portion for holding a guidewire therein, and a proximal body having a solution lumen.

More specifically, the present invention is directed to a microcatheter which is designed to hold solution such as a contrast solution or a therapeutic or diagnostic solution in a proximal lumen, and simultaneously hold a guidewire in a distal tip lumen, and which can be used to inject solution into a vessel while manipulating the guidewire or the microcatheter in the vessel.

BACKGROUND

Microcatheters are commonly used by physicians to access discreet regions of the arterial vasculature during interventional procedures. They are typically used to facilitate the placement and exchange of guidewires, and may also be used to subselectively infuse or deliver therapeutic agents. Some examples of microcatheters are Skyway® and Minnie® (Vascular Solutions, Inc.), Rebar®, Nautica™ and Echelon™ (ev3, Inc.), Quick-Cross® Select (Spectranetics, Inc.), Tracker® Excel™ (Boston Scientific, Inc.) and Corsair® (Asahi Intecc) all of which are single lumen catheters, with the lumen sized to have a substantially close fit with a guidewire placed therethrough in order to provide support to the guidewire. These devices may be comprised of a single or multiple-layer polymer shaft, or a polymer shaft with a stainless steel braid. To perform perfusion of diagnostic or therapeutic agents, the guidewire must be removed from the lumen, and this may result in a loss of access to the distal vasculature.

SUMMARY OF THE INVENTION

There is provided, in accordance with embodiments of the present invention, a microcatheter. The microcatheter includes an elongate tubular body having a body proximal end, a body distal end and a solution lumen extending axially through the elongate tubular body. The elongate tubular body has an outlet port at the body distal end. The microcatheter further includes a tip portion having a tip portion proximal end, a tip portion distal end, and a tip portion lumen extending axially through the tip portion. The tip portion lumen is sized for a substantially close fit for a guidewire to be held therein and has a diameter which is smaller than a diameter of the elongate tubular body.

In accordance with further features in embodiments of the invention, the microcatheter may further include a spine wire extending along a length of the elongate tubular body and bonded thereto and further at least partially connected to the tip portion. The tip portion proximal end may be positioned distal to the outlet port of the elongate tubular body. In some embodiments, the elongate tubular body is continuous with the tip portion and configured to hold a proximal portion of the guidewire therein. In other embodiments, the tip portion is separate from the tubular body, and may be eccentric thereto. In some embodiments, the tip portion has a proximal opening at the tip portion proximal end, and the proximal opening is not co-linear with the outlet port. The tip portion may be at least partially radiopaque, and may have a length of 10 mm-120 mm. An inner diameter of the tip portion may be approximately 0.002" larger than a diameter of a guidewire to be placed therethrough, or may be any size such that a tight fit is provided around the guidewire. In some embodiments, a balloon may be positioned on the distal tip portion, wherein the balloon may be made of a compliant material, or a semi-compliant material, depending on the application. The balloon may be positioned on a proximal end of the tip portion, on a distal end of the tip portion, or anywhere in between depending on the application.

There is provided, in accordance with another embodiment of the present invention, a microcatheter. The microcatheter includes an elongate tubular body having a body proximal end, a body distal end, and a solution lumen extending axially through said elongate tubular body, the elongate tubular body having an outlet port at the body distal end, and a tip portion having a tip portion proximal end, a tip portion distal end, and a tip portion lumen extending axially through the tip portion, the tip portion lumen sized for a substantially close fit for a guidewire to be held therein, wherein the tip portion has a proximal opening at the tip portion proximal end and wherein the tip portion is eccentric to the elongate tubular body and wherein the proximal opening of the tip portion is not co-linear with the outlet port.

In accordance with further features in embodiments of the present invention, the elongate tubular body and the tip portion may have substantially the same diameter or may have different diameters. The tip portion proximal end is positioned distal to the outlet port of the elongate tubular body. The tip portion may be at least partially radiopaque, and in some embodiments, the tip portion is comprised of a polymer compounded with radiopaque material. The tip portion may be in a range of 10 mm to 120 mm long. An inner diameter of the tip portion may be approximately 0.002" larger than a diameter of a guidewire to be placed therethrough.

There is provided, in accordance with another embodiment of the present invention, a method for providing a solution to a portion of a vessel. The method includes providing a microcatheter having an elongate tubular body with a lumen extending axially therethrough and an outlet port, and a tip portion distal to the elongate tubular body, the tip portion having a tip portion lumen extending axially therethrough. The method includes placing a guidewire in the vessel, advancing the microcatheter into the vessel by placing the guidewire through at least the tip portion of the microcatheter and advancing the microcatheter over the guidewire, introducing solution into the elongate tubular body at the body proximal end, and injecting the solution into the vessel through the outlet port.

According to further features in embodiments of the present invention, the solution may be a contrast solution, a therapeutic solution, a diagnostic solution, or any other solution which may be introduced into a vessel. The method may include alternately injecting the solution and advancing the guidewire in the vessel. In some embodiments, the injecting may be done in short puffs. In some embodiments, the guidewire is placed through both the elongate tubular body and the tip portion, and the solution is injected into the elongate tubular body with the guidewire therein. In other embodiments, the tip portion is separate from the elongate tubular body, and the guidewire is placed only through the tip portion. In some embodiments, the guidewire may be exchanged by using the tip portion as a rapid exchange distal rail.

There is provided, in accordance with yet another embodiment of the present invention, a method for crossing an occlusion in a vessel. The method includes advancing a retrograde guidewire into the vessel from the retrograde direction, advancing an antegrade guidewire into the vessel from the antegrade direction, advancing a catheter over the antegrade guidewire, the catheter including a compliant balloon positioned at its distal end, removing the antegrade guidewire from the catheter, inflating the balloon, pulling the catheter proximally, thereby forming a funnel shape in the balloon, and advancing the retrograde guidewire through the balloon and into the catheter.

Unless otherwise defined, all technical and scientific terms used herein have the same meaning as commonly understood by one of ordinary skill in the art to which this invention belongs. Although methods and materials similar or equivalent to those described herein can be used in the practice or testing of the embodiments of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of various embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several embodiments of the invention may be embodied in practice.

In the drawings.

Figure 1:
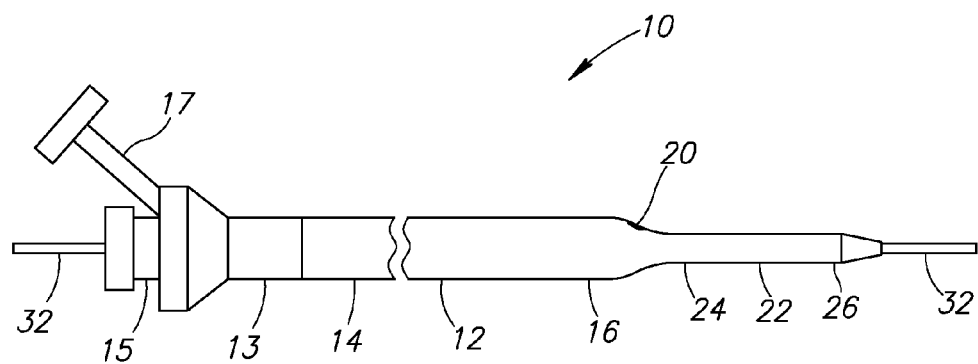
FIG. 1 is a schematic illustration of a microcatheter in accordance with embodiments of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

In the following detailed description, numerous specific details are set forth in order to provide a thorough understanding of the present invention. It will be understood by those of ordinary skill in the art that embodiments of the present invention may be practiced without these specific details. In other instances, well-known methods, procedures, components and structures may not have been described in detail so as not to obscure the present invention.

The present invention relates to a microcatheter having a proximal solution lumen and methods of use thereof. The microcatheter of the present invention allows for injection of solution into a vessel with a guidewire in the vessel at the same time. When the solution is a contrast solution, the design of the present invention allows for enhanced viewing as the wire is advanced, and also provides minimization of contrast solution used. Further advantages of the design of the microcatheter of the present invention will be described hereinbelow.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Reference is now made to FIG. 1, which is a schematic illustration of a microcatheter 10 in accordance with embodiments of the present invention. Microcatheter 10 has an elongate tubular body 12 having a body proximal end 14 and a body distal end 16. Body proximal end 14 is connected to an introduction port 13 which can be used for introduction of a solution, such as contrast solution, and for introduction of a guidewire into microcatheter 10. Introduction port 13 may include a guidewire port 15 for introduction of a guidewire 32 therethrough and a solution port 17 for introduction of solution. A tip portion 22 is positioned distal to body distal end 16. Tip portion 22 may be continuous with elongate tubular body 12 or may be separated therefrom, as will be described in further detail thereinbelow. An outlet port 20 is positioned at body distal end 16, proximal to tip portion 22. Outlet port 20 may comprise one or multiple openings. Tip portion 22 has a tip portion proximal end 24, and a tip portion distal end 26. Tip portion 22 has a length of between 10 mm and 120 mm. Tip portion 22 is sized to snugly fit a guidewire therethrough along the entire length of tip portion 22. Thus, tip portion 22 may have an inner diameter on an order of approximately 0.002" bigger than a diameter of a guidewire to be placed therethrough so as to obtain a tight fit. For example, tip portion 22 may have an inner diameter of 0.016" for positioning of a 0.014" diameter guidewire therethrough, or tip portion 22 may have an inner diameter of 0.020" for positioning of a 0.018" guidewire therethrough, or tip portion 22 may have an inner diameter of 0.037" for positioning of a 0.035" guidewire therethrough. It should be readily apparent that tip portion 22 may have other diameters, provided that a guidewire fits snugly inside. The tight fit for the guidewire provides for minimization of the distal portion of microcatheter 10 and enhanced pushability and maneuverability of the guidewire. In addition, in some embodiments, the tight fit also acts as a seal so that a solution introduced through elongate tubular body 20 will exit through outlet port 20 and not through tip portion 22. A guidewire 32 is shown positioned within microcatheter 10 and extending through tip portion 22.

Elongate tubular body 12 may have various embodiments, as will be described with reference to FIGS. 2-5 hereinbelow. In all of the embodiments, elongate tubular body 12 includes a solution lumen, for introducing contrast solution, or medications or other types of solutions into the vessel. In some embodiments, the same lumen is used for guidewire 32, while in other embodiments, a separate lumen is used for guidewire 32. In some embodiments, guidewire 32 is positioned through tip portion 22 only, and not through elongate tubular body 12. In all of the embodiments, guidewire 32 is positionable through at least tip portion 22.

Figure 2:
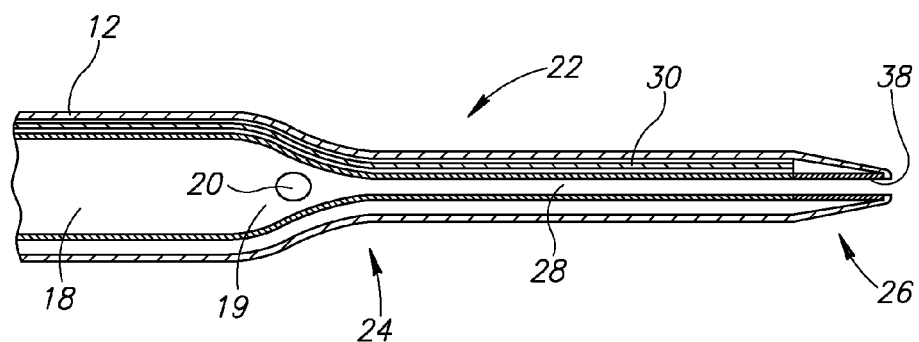
FIG. 2 is a cross-sectional illustration of a distal portion of the microcatheter of FIG. 1, in accordance with embodiments of the present invention.

Reference is now made to FIG. 2, which is a cross-sectional illustration of a distal portion of mircrocatheter 10, in accordance with embodiments of the present invention. In the embodiment shown in FIG. 2, elongate tubular body 12 comprises a solution lumen 18 having a diameter which is sufficiently wide to accommodate both guidewire 32 and a solution to be introduced into the vessel. Solution lumen 18 has a solution lumen proximal end (not shown) which is in fluid communication with introduction port 13, and a solution lumen distal end 19 having outlet port 20 at a distal end thereof. Outlet port 20 may comprise one or multiple openings. Tip portion 22 has a tip portion lumen 28 extending from tip portion proximal end 24 to tip portion distal end 26. Guidewire 32 (not shown) may be positioned through solution lumen 18 and further through tip portion lumen 28 and out through tip portion distal end 26. Guidewire 32 positioned through tip portion 22 essentially seals tip portion 22, such that a solution introduced through solution lumen 18 while a guidewire is in place exits via outlet port 20 at body distal end 16. Thus, it is possible to introduce a solution, such as contrast solution, for example, into the vessel while simultaneously manipulating guidewire 32 and microcatheter 10 within the vessel.

An additional feature of microcatheter 10 includes a spine wire 30 embedded within a wall of microcatheter 10. Spine wire 30 is a spring tempered 304 stainless steel wire having a stiffer proximal end (0.015" outer diameter) and a more flexible distal end, tapering to a dimension of 0.003". Thus, spine wire 30 is both a stiff and a flexible wire which runs along tip portion 22 and elongate tubular body 12 of microcatheter 10. Elongate tubular body 12 may be comprised of a polymeric material, such as nylon, and thus has flexibility for advancement through the vessel, but may not have sufficient stiffness for pushability and torqueability. Thus, spine wire 30 provides stiffness to elongate tubular body 12 to enhance pushability and torqueability of microcatheter 10. Moreover, spine wire 30 has a tapered distal end to provide increased flexibility while maintaining and transmitting the push and torque properties of elongate tubular body 12 to a distal tip of microcatheter 10.

Microcatheter 10 may further comprise at least one radiopaque marker 38 included in tip portion 22. Radiopaque marker 38 is comprised of any radiopaque material, such as tungsten, platinum/iridium or gold, for example, and is embedded within tip portion 22 so that a position of tip portion 22 in the vessel can be viewed. In another embodiment, tip portion 22 is itself comprised of radiopaque material. This can be done, for example, by compounding a polymer with radiopaque material.

Figure 3:
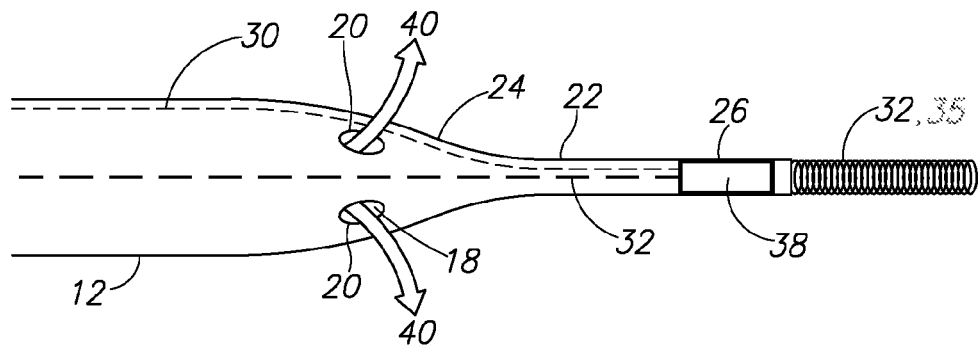
FIG. 3 is a schematic illustration of a distal portion of the microcatheter of FIG. 1, with a guidewire 32 in place and with solution being pushed through an outlet port in accordance with embodiments of the present invention.

Reference is now made to FIG. 3, which is a schematic illustration of a distal portion of microcatheter 10 with guidewire 32 in place through solution lumen 18 and through tip portion 22, and with solution being pushed through outlet port 20. Elongate tubular body 12 is shown with spine wire 30 (shown in thin dotted lines) embedded therein. Solution lumen 18 holds both solution and guidewire 32. Guidewire 32 is shown inside solution lumen 18 (with thick dotted lines), inside tip portion 22 (with thick dotted lines) and extending distally outside of tip portion 22. Solution is depicted via arrows 40 exiting via outlet port 20. As depicted in FIG. 3, tip portion 22 is sized to provide support to guidewire 32 positioned therein by providing a close fit for guidewire 32 along an entire length of tip portion 22. A distal portion 35 of guidewire 32 is shown just distally past tip portion 22.

Figure 4A:
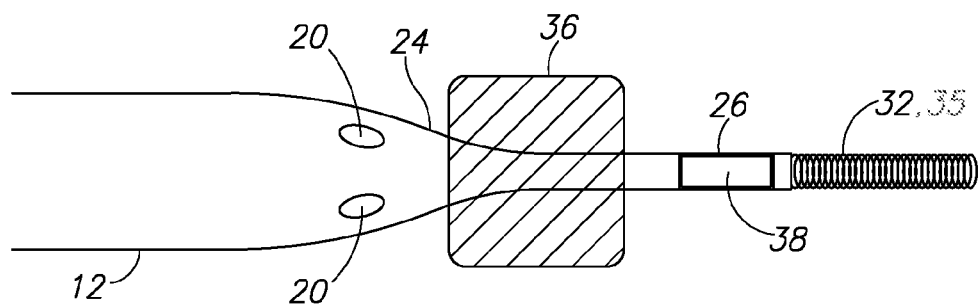
FIGS. 4A and 4B are schematic illustrations of a distal portion of the microcatheter having a balloon, in accordance with another embodiment of the present invention.
Figure 4B:
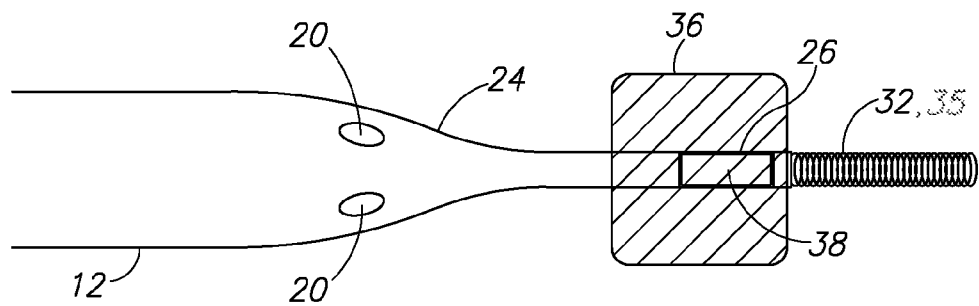

Reference is now made to FIGS. 4A and 4B, which are schematic illustrations of a distal portion of microcatheter 10 in accordance with another embodiment of the present invention. In this embodiment, a balloon 36 is positioned on tip portion 22. Balloon 36 may be at proximal end 24 of tip portion 22, as shown in FIG. 4A, or at distal end 26 of tip portion 22, as shown in FIG. 4B, or at any point in between, depending on the application. An additional inflation lumen may be added for introduction of inflation fluid into balloon 36 for expansion of balloon 36. In this case, an inflation port would be added to introduction port 13 at proximal end 14 of microcatheter 10. Balloon 36 may be a compliant or semi-compliant balloon, both types of which are commonly known in the art. The embodiment shown in FIG. 4A, when used with a semi-compliant balloon in particular, is suitable, for example, for treating a chronic total occlusion (CTO). In a case of CTO, balloon 36 can be used to break up the lesion and then advance guidewire 32 through the lesion, while simultaneously injecting contrast solution through outlet port 20 to view advancement of guidewire 32. The embodiment shown in FIG. 4B, when used with a compliant balloon, may be suitable for retrograde pedal artery access. Generally, in such procedures, a hollow needle is placed in the foot, advanced to the femoral artery, and a guidewire is advanced through the hollow needle. A sheath is introduced from above the blockage through the femoral artery. The guidewire is further advanced through the hollow needle to be placed through the sheath and to then be pushed through the lesion. However, it is difficult to thread the guidewire into the sheath, particularly because the sheath is generally relatively short. The microcatheter of the present invention can be used instead of a sheath, and may be advanced to the blockage area. The compliant balloon 36 can then be pulled back and used as a funnel to catch the guidewire coming from the hollow needle, as will be described in greater detail hereinbelow.

Figure 5A:
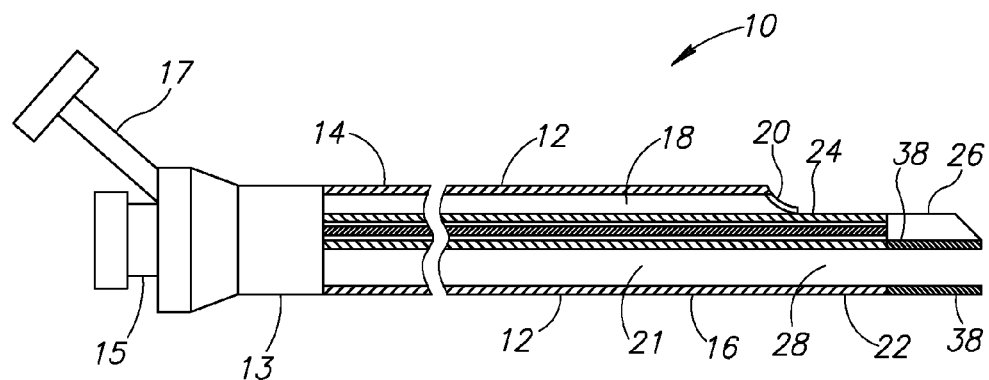
FIGS. 5A and 5B are cross-sectional illustrations of a microcatheter in accordance with an additional embodiment of the present invention.
Figure 5B:
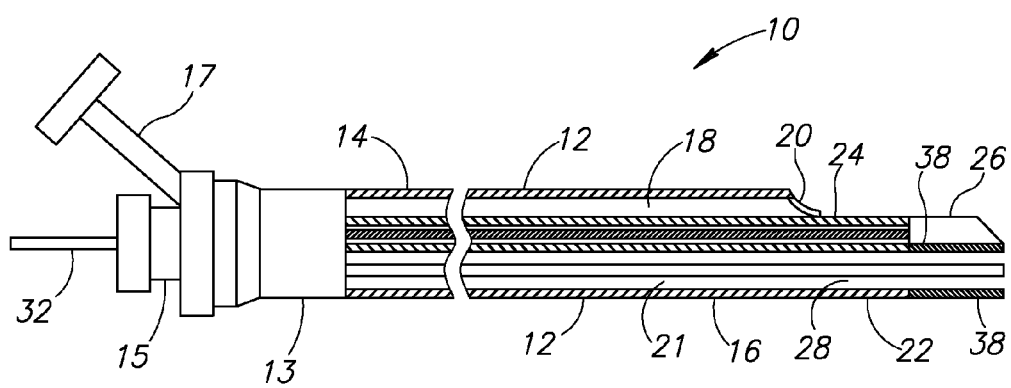

Reference is now made to FIGS. 5A and 5B, which are cross-sectional illustrations of microcatheter 10 in accordance with an additional embodiment of the present invention. Microcatheter 10 has an elongate tubular body 12 having a body proximal end 14 and a body distal end 16. Body proximal end 14 is connected to an introduction port 13 which can be used for introduction of a solution through solution port 17, such as contrast solution, and for introduction of a guidewire through guidewire port 15, into microcatheter 10. A tip portion 22 is positioned distal to body distal end 16. Tip portion 22 is continuous with elongate tubular body 12. An outlet port 20 is positioned at body distal end 16, proximal to tip portion 22. Outlet port 20 may comprise one or multiple openings. Tip portion 22 has a tip portion proximal end 24, and a tip portion distal end 26. Tip portion 22 has a length of between 10 mm and 120 mm. Tip portion 22 is sized to snugly fit a guidewire therethrough and may further include a radiopaque marker 38.

In the embodiment shown in FIGS. 5A and 5B, elongate tubular body 12 comprises a solution lumen 18 and a separate guidewire lumen 21, wherein guidewire lumen 21 leads directly into tip portion lumen 28 so that a guidewire 32 may be positioned through elongate tubular body 12 and directly into tip portion 22. A view of microcatheter 10 in accordance with this embodiment is shown in FIG. 5B with guidewire 32 positioned therein. Solution lumen 18 extends from elongate tubular body proximal end 14 to elongate tubular body distal end 16 and ends distally in outlet port 20. Thus, a solution is introduced through solution lumen 18 which runs alongside but is separated from guidewire lumen 21. Spine wire 30 is embedded within elongate tubular body 12 and may extend distally through tip portion 22. Thus, it is possible to introduce a solution, such as contrast solution, for example, into the vessel while simultaneously manipulating guidewire 32 and microcatheter 10 within the vessel.

Figure 6A:
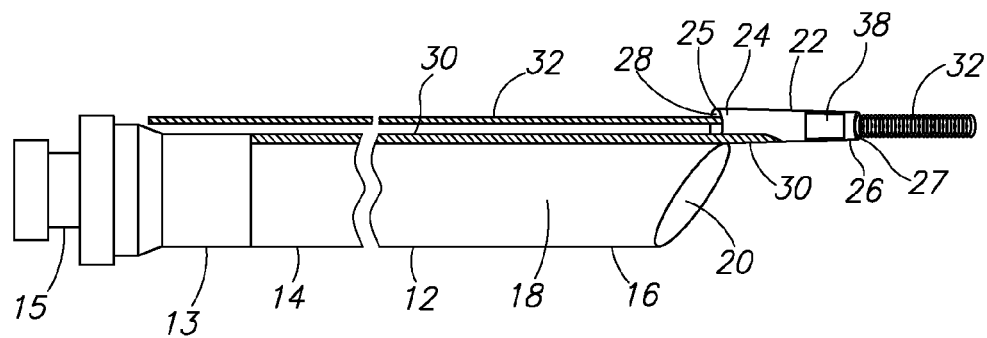
FIGS. 6A and 6B are schematic illustrations of a microcatheter in accordance with yet another embodiment of the present invention.
Figure 6B:
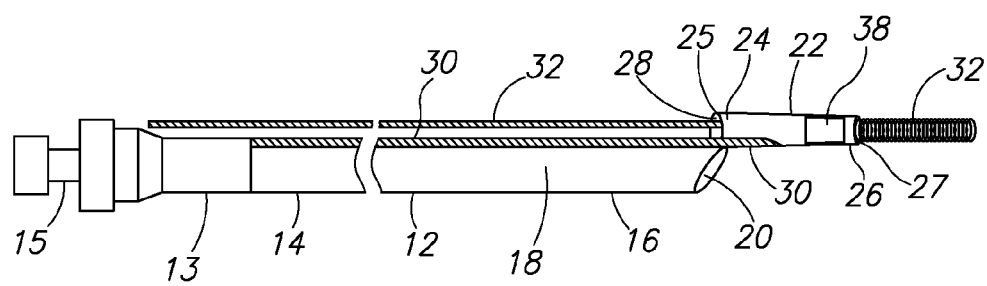

Reference is now made to FIGS. 6A and 6B, which are schematic illustrations of a microcatheter 10 in accordance with yet another embodiment of the present invention. Microcatheter 10 has an elongate tubular body 12 having a body proximal end 14 and a body distal end 16. Body proximal end 14 is connected to an introduction port 13 which can be used for introduction of a solution, such as contrast solution. Elongate tubular body 12 comprises a solution lumen 18. A separate tip portion 22 is connected to distal end 16 of elongate tubular body 12, and has a separate tip portion lumen 28. Tip portion 22 is separated from and eccentric to elongate tubular body 12. Tip portion 22 may be described as a distal rail, attached to body distal end 16. An outlet port 20 is positioned at body distal end 16, wherein outlet port 20 is an opening from solution lumen 18 into the vessel. Tip portion 22 has a tip portion proximal end 24, and a tip portion distal end 26 and a radiopaque marker 38. Tip portion 22 has a length of between 10 mm and 30 mm or any length suitable for rapid exchange of wires. Tip portion 22 is sized to snugly fit a guidewire therethrough.

Guidewire 32 is positioned only in tip portion lumen 28, and not in solution lumen 18. Solution lumen 18 is reserved for introduction of solution therethrough. In this embodiment, tip portion 22 has a proximal opening 25 at tip portion proximal end 24 and a distal opening 27 at tip portion distal end 26. Proximal opening 25 is not co-linear with outlet port 20. Guidewire 32 is introduced directly into tip portion lumen 28, and not through introduction port 13. In this embodiment, introduction port 13 may not include guidewire port 17. Spine wire 30 is embedded within elongate tubular body 12 and may extend distally to tip portion 22. Thus, it is possible to introduce a solution, such as contrast solution, for example, into the vessel while simultaneously manipulating guidewire 32 and microcatheter 10 within the vessel.

In one embodiment, as shown in FIG. 6A, tip portion 22 and elongate tubular body 12 have different diameters. Thus, if desired, different sized wires may be introduced through each of tip portion lumen 28 and solution lumen 18. In another embodiment, as shown in FIG. 6B, tip portion 22 and elongate tubular body 12 have substantially the same diameter. In this embodiment, wires having the same size may be introduced through each of tip portion lumen 28 and solution lumen 18.

Figure 7A:
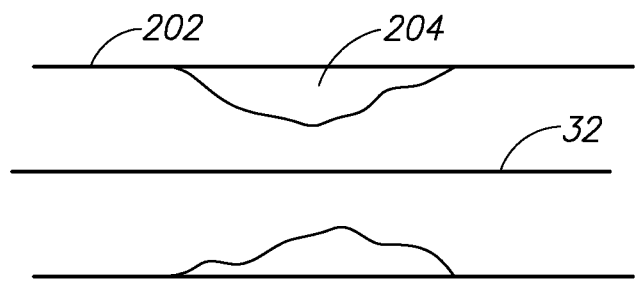
FIGS. 7A-7D are schematic illustrations of steps of a method of providing a solution to a portion of a vessel, in accordance with embodiments of the present invention.
Figure 7B:
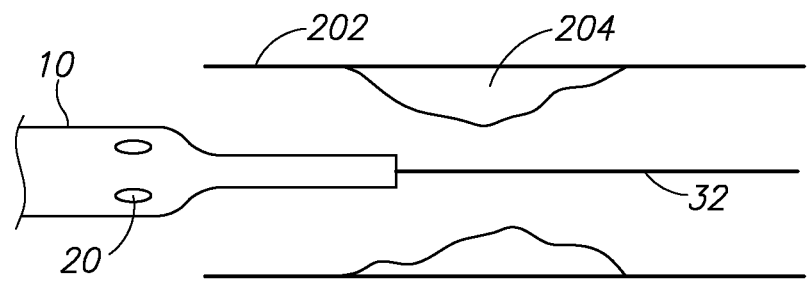

Reference is now made to FIGS. 7A-7D, which are schematic illustrations of a method of using microcatheter 10 in accordance with embodiments of the present invention. First, as shown in FIG. 7A, guidewire 32 is introduced into a vessel 202. In some embodiments, an occlusion 204 may be present in vessel 202, and microcatheter 10 is used to treat occlusion 204. Next, as shown in FIG. 7B, microcatheter 10 is introduced over guidewire 32 into vessel 202. Although the embodiment shown in FIGS. 7A-7D depict microcatheter 10 in accordance with the embodiments shown in FIGS. 1-5 of the present application, it should be readily apparent that microcatheter 10 in accordance with the embodiment shown in FIG. 6, or any other embodiments of microcatheter 10 which are included within the scope of the present invention, may be used for the method shown in FIGS. 7A-7D.

Figure 7C:
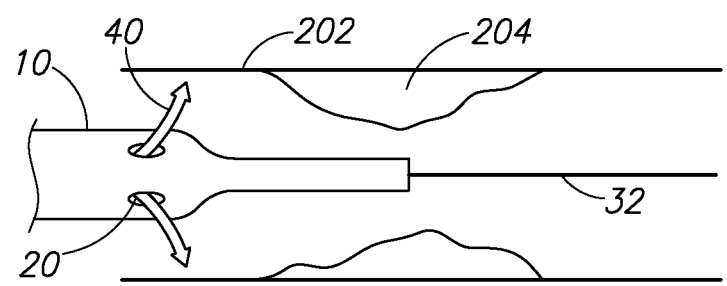
Figure 7D:
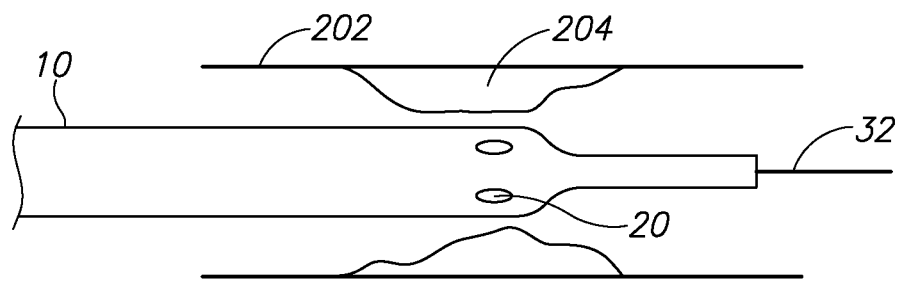

Once microcatheter 10 is advanced, a solution, shown by arrows 40, may be introduced into vessel 202, as shown in FIG. 7C. The solution may be, for example, a contrast solution for internal viewing of vessel 202. Alternatively, the solution may be a diagnostic or therapeutic solution for treatment of occlusion 204. A particular advantage of the design of microcatheter 10 is that the solution may be stored within solution lumen 18 of microcatheter 18, and introduced into vessel 202 only when needed, and in variable amounts. For example, contrast solution may be stored in solution lumen 18, and introduced into vessel 202 in short puffs so as to minimize exposure to the potentially harmful solution. In this way, microcatheter 10 and guidewire 32 may be advanced and viewed, either alternatingly or simultaneously or in any other sequence, so as to maximize viewing and minimize exposure to contrast solution. Thus, in a first configuration the distal end of the movable guidewire is in a first position with respect to the tip portion and in a second configuration the distal end of the movable guidewire is in a second position with respect to the tip portion, wherein the second position is distal to the first position, such that the guidewire may be advanced within the vessel past the tip portion while also being supported by the tip portion. Similarly, when the solution is a therapeutic or diagnostic solution, the amount introduced into vessel 202 may be varied in real time, depending on factors taken into account at the time of the procedure. Such factors may include, for example, the composition or size of occlusion 204, or other factors. Advancement of microcatheter 10 is shown in FIG. 7D. Another advantage of the present invention is that guidewire 32 can occlude tip portion 22 due to its tight fit, thus enabling the solution to enter the vessel only via outlet port 20.

Figure 8:
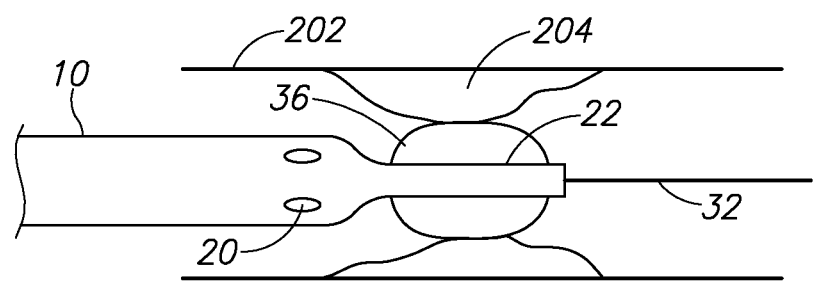
FIG. 8 is a schematic illustration of an additional method step in accordance with embodiments of the present invention.

Reference is now made to FIG. 8, which is a schematic illustration of microcatheter 10 with a balloon 36 on tip portion 22. Tip portion 22 may be advanced into an area of vessel 202 having occlusion 204, and balloon 36 may be expanded to break up occlusion 204. The remaining steps of introducing solution and manipulating the guidewire may be done in this embodiment as well.

Figure 9A:
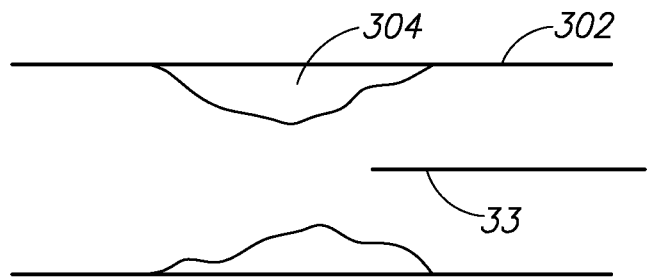
FIGS. 9A-9F are schematic illustrations of steps of a method of crossing a lesion in a vessel, in accordance with additional embodiments of the present invention.
Figure 9B:
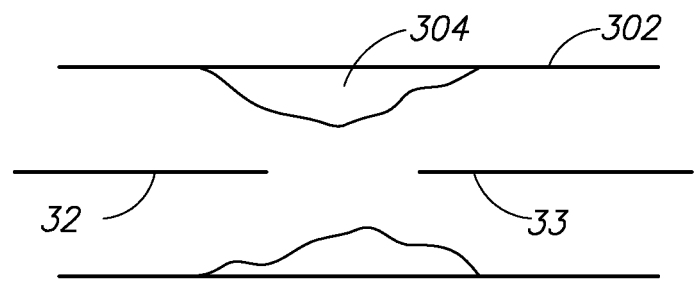
Figure 9C:
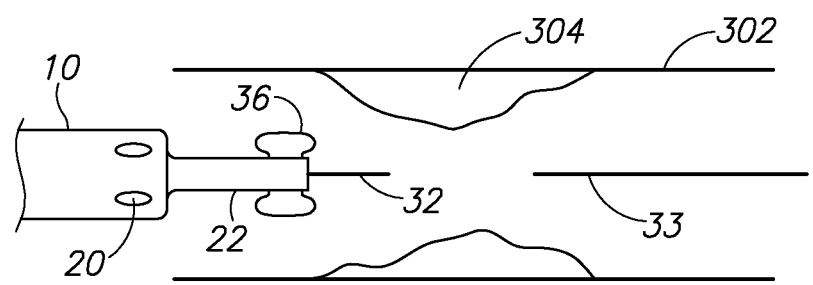
Figure 9D:
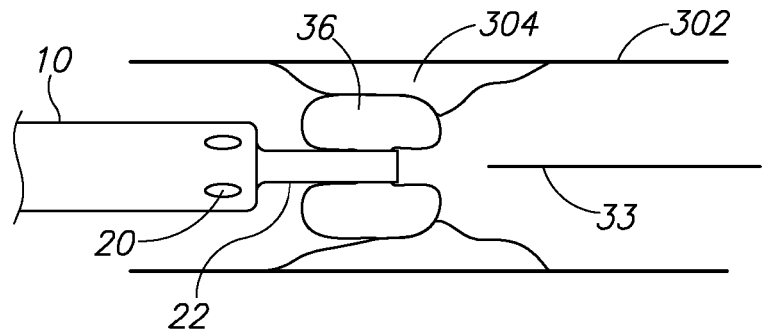
Figure 9E:
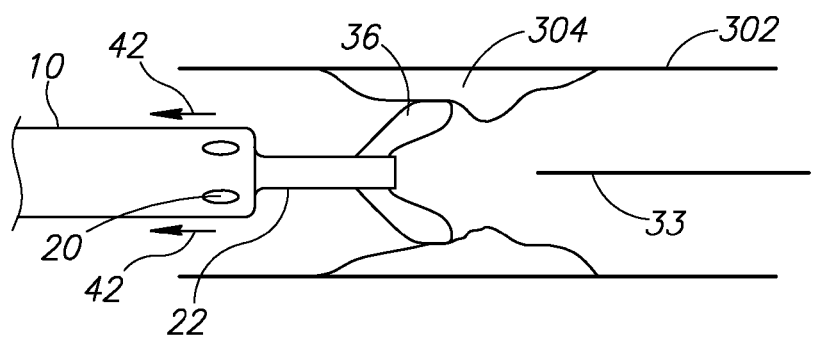
Figure 9F:
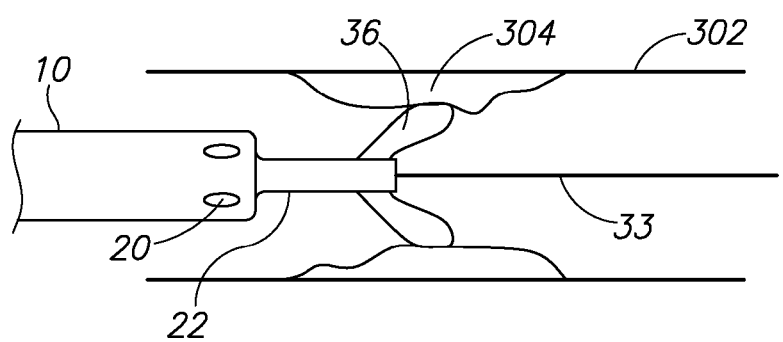

Reference is now made to FIGS. 9A-9F, which are schematic illustrations of a method of using microcatheter 10 for retrograde access of an artery such as a pedal artery, for example. It should be readily apparent that any catheter having a compliant balloon on its distal end may be used in the present method, and not just a microcatheter as described. As shown in FIG. 9A, first a retrograde guidewire 33 is advanced into a vessel 302 having an occlusion 304. Retrograde guidewire 33 is introduced into vessel 302 from a retrograde direction, via a hollow needle 400, for example. Next, a guidewire 32 is advanced into vessel 302 from an antegrade direction, as shown in FIG. 9B. Next, microcatheter 10, or any other suitable catheter, having balloon 36 on tip portion 22 is advanced over guidewire 32. Balloon 36 is a compliant balloon, and is positioned at a distal portion of tip portion 22. As described above with reference to FIGS. 7A-7D, solution may be introduced through outlet port 20 during any point in the advancement of microcatheter 10 into vessel 302. When microcatheter 10 is in place on the antegrade side of occlusion 304, guidewire 32 is removed from microcatheter 10, and balloon 36 is expanded, as shown in FIG. 9D. Next, as shown in FIG. 9E, microcatheter 10 is pulled back proximally, shown by arrows 42, and due to the compliant property of balloon 36, balloon 36 forms a funnel shape within the vessel 302 and/or within the occlusion 304. Next, as shown in FIG. 9F, retrograde guidewire 33 may be advanced through occlusion 304 and into tip portion 22 of microcatheter 10. Because of the funnel-shape of balloon 36, it is relatively easy to find the opening in tip portion 22. Retrograde guidewire 33 may be comprised of a flexible material and/or design (e.g. coil springs) so as not to puncture balloon 36. It should be readily apparent that guidewire 32 may alternatively be removed from microcatheter 10 just before advancement of retrograde guidewire 33. Once retrograde guidewire 33 is in microcatheter 10, retrograde guidewire 33 may be advanced proximally through microcatheter 10, and then used to replace guidewire 32 for the procedure to follow.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A microcatheter for providing support to advance a movable guidewire through a vessel or an occlusion within the vessel and for simultaneously providing means for local perfusion of a solution, the microcatheter comprising:

an elongate tubular body having a body proximal end, a body distal end and a solution lumen extending axially through said elongate tubular body, said elongate tubular body having a body inner diameter, said elongate tubular body comprising an outlet port at said body distal end, said outlet port configured to introduce a solution from said solution lumen into a vessel;

a tip portion continuous with and distal to said elongate tubular body, said tip portion having a tip portion proximal end distal to said outlet port, a tip portion distal end and a tip portion lumen extending axially through said tip portion, wherein said tip portion lumen is continuous with said solution lumen, wherein said tip portion has a length extending from said tip portion proximal end to said tip portion distal end of at least 10 mm and a tip portion inner diameter which is smaller than said body inner diameter; and a movable guidewire positioned within said tip portion, the movable guidewire having a distal end, wherein entirely along said length of said tip portion, said tip portion lumen is sized for a substantially close fit for the movable guidewire to be held therein thus providing support and enhanced pushability to the movable guidewire, wherein in a first configuration the distal end of the movable guidewire is in a first position with respect to the tip portion and in a second configuration the distal end of the movable guidewire is in a second position with respect to the tip portion, wherein the second position is distal to the first position, such that the guidewire may be advanced and manipulated within the vessel past the tip portion while also being supported by the tip portion, and such that when said movable guidewire is positioned within said tip portion, solution from said solution lumen is configured to exit through said outlet port and into the vessel.

2. The microcatheter of claim 1, wherein said elongated tubular body is configured to hold a proximal portion of the guidewire therein.

3. The microcatheter of claim 1, wherein said tip portion is separate from said elongated tubular body.

4. The microcatheter of claim 3, wherein said tip portion is eccentric to said elongate tubular body.

5. The microcatheter of claim 1, wherein said tip portion has a proximal opening at said tip portion proximal end, and wherein said proximal opening is not co-linear with said outlet port.

6. The microcatheter of claim 1, wherein said tip portion is at least partially radiopaque.

7. The microcatheter of claim 6, wherein said tip portion is comprised of a polymer compounded with radiopaque material.

8. The microcatheter of claim 1, wherein said tip portion is in a range of 10 mm to 120 mm long.

9. The microcatheter of claim 1, wherein said tip portion inner diameter is approximately 0.002" larger than a diameter of a guidewire to be placed therethrough.

10. The microcatheter of claim 1, wherein said outlet port comprises multiple openings.

11. The microcatheter of claim 1, wherein said outlet port comprises an opening at said body distal end, wherein said opening leads directly into the vessel.

12. The microcatheter of claim 1, further comprising a balloon positioned on said tip portion.

13. The microcatheter of claim 12, wherein said balloon is comprised of a compliant material.

14. The microcatheter of claim 12, wherein said balloon is comprised of a semi-compliant material.

15. The microcatheter of claim 1, further comprising a spine wire extending along a length of said elongate tubular body and bonded thereto, said spine wire further at least partially connected to said tip portion.

16. The microcatheter of claim 15, wherein the spine wire has a tapered distal end.

17. The microcatheter of claim 1, wherein said tip portion is in a range of 10 mm to 90 mm long.

18. A method for providing support for manipulating a moveable guidewire and simultaneously providing solution to a portion of a vessel, the method comprising:

providing a microcatheter having an elongate tubular body having a body proximal end and a body distal end with a body lumen extending axially therethrough and an outlet port at a distal end thereof, and a tip portion distal to said elongate tubular body and to said outlet port, said tip portion having a tip portion proximal end and a tip portion distal end, said tip portion having a tip portion lumen extending axially therethrough wherein said tip portion lumen is a continuation of the body lumen and wherein said tip portion lumen has a smaller diameter than a diameter of said body lumen, and wherein the tip portion is sized to provide support to a movable guidewire placed therein by providing a close fit for the movable guidewire along an entire length of the tip portion wherein the length of the tip portion extends from said tip portion proximal end to said tip portion distal end, wherein the tip portion is at least 10 mm in length;

placing the movable guidewire in the vessel;

advancing the microcatheter into the vessel by placing the movable guidewire through at least the tip portion of the microcatheter and advancing the microcatheter over the movable guidewire;

introducing solution into said elongate tubular body at said body proximal end with the movable guidewire still positioned within the tip portion;

injecting said solution into the vessel through said outlet port with the movable guidewire still positioned within the tip portion, wherein said injecting is done while minimizing overall exposure to the solution; and advancing the movable guidewire distally from the microcatheter further into the vessel wherein the movable guidewire is supported by the tip portion during said advancing the movable guidewire.

19. The method of claim 18, wherein said solution is contrast solution.

20. The method of claim 18, wherein said solution is a therapeutic or diagnostic solution.

21. The method of claim 18, further comprising simultaneously injecting the solution and advancing the guidewire in the vessel.

22. The method of claim 18, wherein said solution is stored in said solution body lumen and wherein said injecting is done in such a way so as to minimize exposure of the vessel to said solution.

23. The method of claim 18, wherein said tip portion is eccentric to said elongate tubular body, and wherein said guidewire is placed only through said tip portion.

24. The method of claim 18, further comprising exchanging the guidewire by using said tip portion as a rapid exchange distal rail.

25. The method of claim 18, further comprising advancing the microcatheter with the movable guidewire positioned within the tip portion of the microcatheter.

26. The method of claim 18, wherein said advancing the movable guidewire comprises advancing the movable guidewire through an occlusion.

* * * * *